United States Patent
Woodward et al.

(10) Patent No.: US 6,187,791 B1
(45) Date of Patent: Feb. 13, 2001

(54) METHOD OF PROVIDING AN ANTIHISTAMINIC EFFECT IN A HEPATICALLY IMPAIRED PATIENT

(75) Inventors: James K. Woodward, Cincinnati; Richard A. Okerholm, West Chester, both of OH (US); Mark G. Eller, Overland Park; Bruce E. McNutt, Olathe, both of KS (US)

(73) Assignee: Merrell Pharmaceuticals Inc., Bridgewater, NJ (US)

( * ) Notice: Under 35 U.S.C. 154(b), the term of this patent shall be extended for 0 days.

This patent is subject to a terminal disclaimer.

(21) Appl. No.: 09/481,404

(22) Filed: Jan. 12, 2000

Related U.S. Application Data

(63) Continuation of application No. 08/397,542, filed on Mar. 2, 1995, now Pat. No. 6,037,353, which is a continuation of application No. 08/248,850, filed on May 25, 1994, now abandoned, which is a continuation of application No. 08/021,745, filed on Feb. 23, 1993, now abandoned, which is a continuation of application No. 07/922,890, filed on Jul. 31, 1992, now abandoned, which is a continuation-in-part of application No. 07/880,801, filed on May 11, 1992, now abandoned.

(51) Int. Cl.$^7$ .................................. A61K 31/445
(52) U.S. Cl. ............................................ 514/317
(58) Field of Search ............................... 514/317

(56) References Cited

U.S. PATENT DOCUMENTS

| | | |
|---|---|---|
| 4,254,129 | 3/1981 | Carr et al. . |
| 4,929,605 | 5/1990 | Domet et al. . |

OTHER PUBLICATIONS

Garteiz et al, Arzneim.–Forsch/Drug Res., 32:1185 (1982).
Monahan et al, J. Am. Med. Assoc., 264:2788 (1990).
SCRIP, vol. 1525, p. 28, Jun. 22, 1990.
SCRIP, vol. 1546, p. 26, Sep. 5, 1990.
SCRIP, vol. 1568, p. 26, Nov. 21, 1990.
Physician's Desk Reference, 46th Ed., 1992, pp. 1349–1350, Medical Economics Data, a division of Medical Economics Co., Inc., Montvale, NJ.
Transcript of Proceedings, Dept. of Health & Human Services, Public Health Service, Food & Drug Admin., Pulmonary–Allergy Drugs Advisory Committee, vol. 1, Rockville, MD, Jun. 11, 1990.
Physician's Desk Reference, 4th Ed., 1993, Supplement A, pp. A119–A121, Medical Economics Data, a division of Medical Economics Co., Inc., Montvale, NJ.
Rampe et al, "Effects of Terfenadine and Its Metabolites on a Delayed Rectifier K+ Channel Cloned from Human Heart," The American Society of Pharmacology and Experimental Therapeutics, Molecular Pharmacology, 44:1240–1245 (1993).

*Primary Examiner*—William R. A. Jarvis
(74) *Attorney, Agent, or Firm*—Pillsbury Madison & Sutro LLP

(57) ABSTRACT

The present invention relates to a method of providing an antihistaminic effect in a hepatically impaired patient in need thereof comprising administering to said patient an effective antihistaminic amount of a compound of the formula

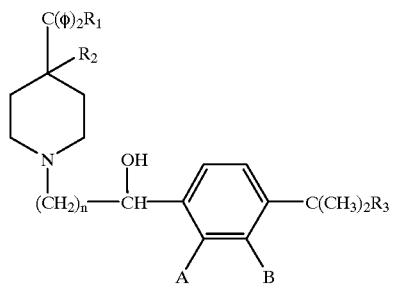

wherein
$R_1$ is hydrogen or hydroxy;
$R_2$ is hydrogen;
or $R_1$ and $R_2$ taken together form a second bond between the carbon atoms bearing $R_1$ and $R_2$;
n is an integer of from 1 to 5;
$R_3$ is —COOH or —COOalkyl wherein the alkyl moiety has from 1 to 6 carbon atoms and is straight or branched;
each of A and B is hydrogen or hydroxy with the proviso that at least one of A or B is hydrogen;
or a pharmaceutically acceptable salt and individual isomers thereof.

9 Claims, No Drawings

METHOD OF PROVIDING AN ANTIHISTAMINIC EFFECT IN A HEPATICALLY IMPAIRED PATIENT

This is a continuation of application Ser. No. 08/397,542, filed Mar. 2, 1996, now U.S. Pat. No. 6,037,353, which is a continuation of appln. Ser. No. 08/248,850, filed May 25, 1994, now abandoned, which is a continuation of appln. Ser. No. 08/021,745, filed Feb. 23, 1993, now abandoned, which is a continuation of appln. Ser. No. 07/922,890, filed Jul. 31, 1992, now abandoned, which is a continuation-in-part of appln. Ser. No. 07/880,801, filed May 11, 1992, now abandoned.

Terfenadine, α-[4-(1,1-dimethylethyl)phenyl]-4-(hydroxydiphenylmethyl)-1-piperidinebutanol, is a known antihistaminic agent which is currently available commercially under the name Seldane® with a recommended dosage of 60 mg B.I.D. (See PHYSICIAN'S DESK REFERENCE, 46th Edition, 1992, pp. 1349–50, Medical Economics Data, a division of Medical Economics Company, Inc., Montvale, N.J. Terfenadine is disclosed in the Carr et al. '217 patent [U.S. Pat. No. 3,878,217, issued Apr. 15, 1975].

Terfenadine undergoes extensive (99%) first pass metabolism to two primary metabolites, an active acid metabolite and an inactive dealkylated metabolite. The active acid metabolite has been identified as 4-[1-hydroxy-4-[4-(hydroxydiphenylmethyl)-1-piperidinyl]butyl]-α,α-dimethyl-benzeneacetic acid. The acid metabolite has been disclosed in the Carr et al. '129 patent [U.S. Pat. No. 4,254,129, issued Mar. 3, 1981] as an antihistaminic agent having oral activity. Studies investigating the effect of hepatic and renal insufficiency on the metabolism and excretion of terfenadine are incomplete.

Preliminary information indicates that in cases of hepatic impairment, significant concentrations of unchanged terfenadine can be detected with the rate of acid metabolite formation being decreased. In subjects with normal hepatic function, unchanged terfenadine plasma concentrations have not been detected.

Recently, it has been found that patients with impaired hepatic function (alcohol cirrhosis, hepatitis), or on ketoconazole or troleandomycin therapy, or having conditions leading to QT prolongation (e.g., hypokalemia, congenital QT syndrome), may experience cardiac events of QT prolongation and/or ventricular tachycardia at the recommended dose of terfenadine.

Surprisingly, it appears that patients with impaired hepatic function who are receiving terfenadine acid metabolite in sufficient amount so as to provide an antihistaminic effect will not experience cardiac events of QT prolongation and/or ventricular tachycardia.

SUMMARY OF THE INVENTION

The present invention relates to a method of providing an antihistaminic effect in a hepatically impaired patient in need thereof comprising administering to said patient an effective antihistaminic amount of a compound of Formula (1)

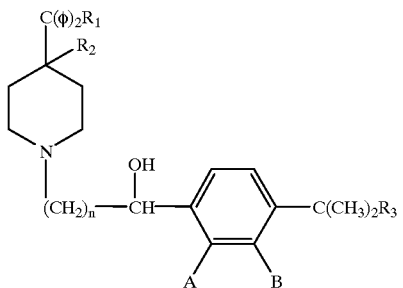

wherein
$R_1$ is hydrogen or hydroxy;
$R_2$ is hydrogen;
or $R_1$ and $R_2$ taken together form a second bond between the carbon atoms bearing $R_1$ and $R_2$;
n is an integer of from 1 to 5;
$R_3$ is —COOH or —COOalkyl wherein the alkyl moiety has from 1 to 6 carbon atoms and is straight or branched;
each of A and B is hydrogen or hydroxy with the proviso that at least one of A or B is hydrogen;
or a pharmaceutically acceptable salt and individual isomers thereof.

DETAILED DESCRIPTION OF THE INVENTION

Compounds of Formula (1), and, in particular, 4-[1-hydroxy-4-[4-(hydroxydiphenylmethyl)-1-piperidinyl]butyl]-α,α-dimethyl-benzeneacetic acid, are prepared and used as described in Carr et al. [U.S. Pat. No. 4,254,129, issued Mar. 3, 1981] which is hereby incorporated herein by reference in its entirety.

The present invention relates to a method of providing an antihistaminic effect in a hepatically impaired patient in need thereof comprising administering to said patient an effective antihistaminic amount of a compound of Formula (1).

The compounds of Formula (1) are known histamine $H_1$-receptor antagonists and as such provide relief of symptoms associated with histamine-mediated diseases and conditions such as seasonal allergic rhinitis, urticaria and the like.

As used herein, the term "patient" refers to a warm-blooded animal, such as a mammal, which is afflicted with a histamine-mediated disease or condition. It is understood that dogs, cats, rats, mice, and humans are examples of animals within the scope of the meaning of the term.

A hepatically impaired patient is a patient having impaired liver function due to disease, such as alcoholic cirrhosis or hepatitis, or due to administration of a drug, such as ketoconazole, erythromycin or troleandomycin, which inhibits normal liver metabolic function. In the hepatically impaired patient, terfenadine is not metabolized at the normal rate to the terfenadine acid metabolite.

When administered terfenadine at the recommended dosage, a hepatically impaired patient will experience increased levels of terfenadine in the blood and decreased levels of the acid metabolite over that expected with the non-hepatically impaired patient. Increased blood levels of terfenadine in turn may cause decreases in the action potential and in various membrane currents of cardiac cells which may trigger cardiac events of QT prolongation and/or ventricular tachycardia. Surprisingly, similar blood levels of the terfenadine acid metabolite do not cause these decreases in the action potential and in various membrane currents of cardiac cells. Therefore, at the same blood levels where terfenadine may trigger cardiac events of QT prolongation and/or ventricular tachycardia, the terfenadine acid metabolite will not trigger these cardiac events.

The identification of those patients who may benefit from the present invention is well within the ability and knowledge of one skilled in the art. A clinician skilled in the art can readily identify, by the use of clinical tests, physical examination and medical/family history, those patients who are hepatically impaired and who are in need of treatment with an antihistamine.

An effective antihistaminic amount of a compound of Formula (I) is an amount which is effective in antagonizing the histamine $H_1$-receptor in a patient in need thereof which results in an antihistaminic effect.

An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective antihistaminic amount of a compound of Formula (I) will generally vary from about 0.01 milligram per kilogram of body weight per day (mg/kg/day) to about 20 mg/kg/day, and will preferably be in the range of about 0.1 to about 6 mg/kg/day. A dose of about 10 mg to about 200 mg two to four times per day is preferred. A dose of about 20 mg to about 180 mg twice per day, or a single daily dose of about 40 mg to about 360 mg, are most preferred.

A compound of Formula (1) can be administered to a patient in any form or mode which makes the compound bioavailable in effective amounts, including oral and parenteral routes. For example, compounds of Formula (1) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

The present invention contemplates compositions comprising a compound of Formula (1) in admixture or otherwise in association with one or more inert carriers. These compositions are useful, for example, as assay standards, as convenient means of making bulk shipments, or as pharmaceutical compositions. An assayable amount of a compound of Formula (1) is an amount which is readily measurable by standard assay procedures and techniques as are well known and appreciated by those skilled in the art. Assayable amounts of a compound of Formula (1) will generally vary from about 0.001% to about 75% of the composition by weight. Inert carriers can be any material which does not degrade or otherwise covalently react with a compound of Formula (1). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention contemplates pharmaceutical compositions comprising a therapeutically effective amount of a compound of Formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel™, corn starch and the like; lubricants such as magnesium stearate or Sterotex™; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 300 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

What is claimed is:

1. A method of treating a histaminic-mediated condition in a patient in need thereof but susceptible to possible cardiac events associated with the administration of terfenadine, said method comprising administering to said patient an effective antihistaminic amount of a compound of the formula:

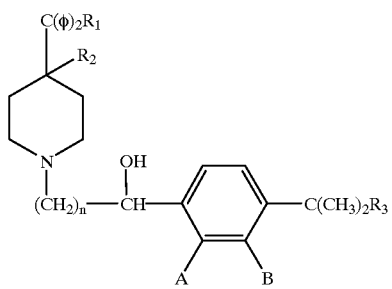

wherein $R_1$ is hydrogen or hydroxy;

$R_2$ is hydrogen;

or $R_1$ and $R_2$ taken together form a second bond between the carbon atoms bearing $R_1$ and $R_2$;

n is an integer of from 1 to 5;

$R_3$ is —COOH or —COOalkyl wherein the alkyl moiety has from 1 to 6 carbon atoms and is straight or branched;

each of A and B is hydrogen or hydroxy with the proviso that at least one of A or B is hydrogen;

or a pharmaceutically acceptable salt and individual enantiomers thereof.

2. A method of claim 1 wherein the compound is 4-[1-hydroxy-4-[4-(hydroxydiphenymethyl)-1-piperidinyl] butyl]-α,α-dimethyl benzeneacetic acid.

3. A method of claim 1 wherein the compound is (R)—4-[1 -hydroxy-4-[4-hydroxydiphenylmethyl)-1 -piperidinyl] butyl]-α,α-dimethyl benzeneacetic acid.

4. A method of claim 1 wherein the compound is (S)-4-[1-hydroxy-4[4-hydroxydiphenylmethyl)-1-piperidinyl] butyl]-α,α-dimethyl benzeneacetic acid.

5. A method of treating a histamine-mediated disease in a human while avoiding the concomitant liability of cardiac arrhythmias associated with the administration of terfenadine, comprising administering to said human a therapeutically effective amount of racemic terfenadine carboxylate or a pharmaceutically acceptable salt thereof.

6. The method of claim 5 wherein the amount of racemic terfenadine carboxylate administered is from about 20 mg to about 800 mg per day.

7. The method of claim 6 wherein the amount of racemic terfenadine carboxylate administered is from about 40 mg to about 360 mg per day.

8. The method of claim 5 wherein the amount of said racemic terfenadine carboxylate or pharmaceutically acceptable salt thereof is administered together with a pharmaceutically acceptable carrier.

9. In a method of providing an antihistaminic effect in a patient susceptible to QT prolongation and/or ventricular tachycardia when using terfenadine, the improvement which comprises administering to said patient an effective amount of a compound of the formula:

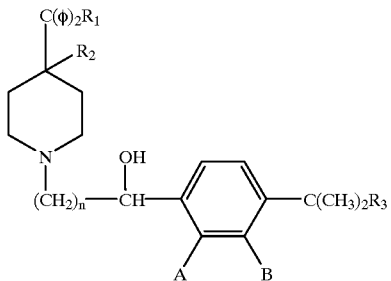

wherein $R_1$ is hydrogen or hydroxy;

$R_2$ is hydrogen;

or $R_1$ and R2 taken together form a second bond between the carbon atoms bearing $R_1$ and $R_2$;

n is an integer of from 1 to 5;

$R_3$ is —COOH or —COOalkyl wherein the alkyl moiety has from 1 to 6 carbon atoms and is straight or branched;

each of A and B is hydrogen or hydroxy with the proviso that at least one of A or B is hydrogen;

or a pharmaceutically acceptable salt and individual enantiomers thereof.

* * * * *